United States Patent [19]

Magnusson et al.

[11] Patent Number: 4,961,707

[45] Date of Patent: Oct. 9, 1990

[54] GUIDED PERIODONTAL TISSUE REGENERATION

[75] Inventors: Ingvar Magnusson, High Springs; Christopher Batich, Gainesville, both of Fla.

[73] Assignee: University of Florida, Gainesville, Fla.

[21] Appl. No.: 362,246

[22] Filed: Jun. 6, 1989

Related U.S. Application Data

[63] Continuation of Ser. No. 136,772, Dec. 22, 1987.

[51] Int. Cl.$^5$ .................. A61C 5/02; A61K 6/00; A61M 31/00
[52] U.S. Cl. .................. 433/215; 128/DIG. 8; 424/424; 424/426; 433/202.1; 433/228.1; 604/285; 604/288
[58] Field of Search ............... 424/422, 424, 426, 443, 424/444; 128/DIG. 8; 433/228.1, 202.1, 215; 604/285, 286, 287, 288, 289, 304

[56] References Cited

U.S. PATENT DOCUMENTS

| | | | |
|---|---|---|---|
| 3,739,773 | 6/1973 | Schmitt et al. | 424/444 |
| 3,887,699 | 6/1975 | Yolles | 128/260 |
| 4,186,448 | 2/1980 | Brekke | 424/426 |
| 4,407,787 | 10/1983 | Stemberger | 424/444 |
| 4,453,939 | 6/1984 | Zimmerman et al. | 604/304 |
| 4,655,980 | 4/1987 | Chu | 128/DIG. 8 |
| 4,702,917 | 10/1987 | Schindler | 424/422 |

FOREIGN PATENT DOCUMENTS

0139318  8/1984  Japan ................... 424/444

OTHER PUBLICATIONS

Chavpil M. et al, "Medical and Surgical Appliances of Collagen" from *International Review of Connective Tissue Research*, vol. 6 1973 pp. 1–6, 9–10, 29–30 and 534.
Gottlow et al, Journal of Clin. Periodon., vol. 11, pp. 494–503 (1984).
Nyman et al, Journal of Clin. Periodon., vol. 9, pp. 257–265, 290–296 (1982).
Magnusson et al, Journal of Periodon Research, vol. 20 pp. 201–208 (1985).
Gottlow et al, Journal of Clin. Periodon., vol. 13, pp. 604–616 (1986).
Greaves et al, Am. Journal Pathol., vol. 120, pp. 207–214 (1985).
Karring et al, Journal of Clin. Periodon., vol. 7, pp. 96–105 (1980).
Isidor et al, Journal of Clin. Periodon., vol. 12, pp. 728–735 (1985).
Melcher, Arch. Oral Biol., vol. 15, pp. 1183–1204 (1979).
Line et al, J. Periodont . vol. 45 (10) pp. 725–(1974).
Melcher, in Biology of the Periodontium, ed. Melcher et al, London, Academic Press (1969).
Boyko et al, Journal of Periodon. Research, vol. 16, pp. 73–88 (1981).
Nyman et al, Journal of Clin. Periodon, vol. 7 pp. 394–401 (1980).
Isidor et al, J. Clin. Periodon., vol. 13 pp 145–150 (1986).
Karring et al, J. Clin. Periodon., vol. 12, pp. 51–60 (1985).
Andreason, Journal of Periodon. Res., vol. 16, pp. 228–235 (1981).
Lindhe et al, Journal of Clin. Periodon., vol. 11, pp. 33–40 (1984).
Caton et al, Journal of Clin. Periodon., vol. 7 pp. 212–223.

*Primary Examiner*—Paul Lieberman
*Assistant Examiner*—Linda J. Skaling
*Attorney, Agent, or Firm*—Kerkam, Stowell, Kondracki & Clarke

[57] ABSTRACT

A method and surgical implant article for enhancing the regeneration of periodontal connective tissue at tooth root surfaces exposed by periodontal surgery wherein the exposed root surfaces are covered with a surgical implant article which is a membrane which excludes contact between the root surfaces and gingival epithelium and gingival connective tissue but permits migration to the root surfaces of PDL cells, the membrane being constructed of a non-toxic, nonimmunogenic, bio-absorbable material.

8 Claims, 1 Drawing Sheet

GUIDED PERIODONTAL TISSUE REGENERATION

This is a continuation of Application Ser. No. 136,722, filed Dec. 22, 1987.

BACKGROUND OF THE INVENTION

Field of the Invention

The invention relates to periodontal surgical methods and surgical implant articles. Prior Art It has been previously proposed to reestablish periodontal connective tissue at exposed root surfaces following periodontal surgery by the principle of guided tissue regeneration. This principle relies for success on utilizing a device which prevents contact between the root surfaces and gingival epithelium and gingival connective tissue and permits the entry of periodontal ligament (PDL) cells into the exposed root area. If the epithelium and connective tissue are allowed to contact the root surfaces during the healing process root resorption and re-epithelialization at the root surface occur, both of which effectively inhibit the regeneration of connective tissue.

For descriptions of prior attempts to achieve guided periodontal tissue regeneration see Gottlow et al, *J. Clin. Periodontol*, Vol. 10, p. 494 (1984); Nyman et al, *J. Clin. Periodontol*, Vol. 9, p. 290 (1982); Nyman et al, *J. Clin. Periodontol*, Vol. 9, p. 257 (1982); Magnusson, et al, *J. Periodont. Res.*, Vol. 20, p. 201 (1985); Gottlow et al, *J. Clin. Periodontol*, Vol. 13, pp. 604-616 (1986); and "GORE-TEX™ PERIODONTAL MATERIAL WORKSHOP MANUAL", W.L. Gore and Associates, Feb. 7, 1987.

These workers utilized Millipore ® filter, teflon and Gore-Tex ® membranes to cover the tooth root during periodontal surgery to prevent contact between the root and the gingival epithelium and connective tissue and thereby allow guided periodontal tissue regeneration by permitting an influx into the root area of substantially only PDL cells.

The space created by the inclusion of these membranes during surgery allows the periodontal ligament to proliferate in a coronal direction. All of these materials suffer from the disadvantage, however, in that they must be removed by a second surgical procedure. There have also been reports that the Millipore ® filters are toxic. See Greaves et al, *Am. J. Pathol.*, Vol. 120, p. 207 (1985).

It is an object of the present invention to provide a novel surgical implant article for guided periodontal tissue regeneration and a method for enhancing the regeneration of periodontal connective tissue after periodontal surgery.

SUMMARY OF THE INVENTION

These and other objects are achieved by the present invention which provides a method of enhancing the regeneration of periodontal connective tissue at root surfaces exposed by periodontal surgery comprising covering the exposed root surfaces with a membrane which excludes contact between the root surfaces and gingival epithelium and gingival connective tissue and permits migration to the root surfaces of PDL cells after surgery, the membrane being constructed substantially of a non-toxic, nonimmunogenic, bio-absorbable material.

The invention further provides a surgical implant article of a size and shape adapted for the guided periodontal connective tissue regeneration at root surfaces exposed by periodontal surgery and consisting essentially of a membrane adapted to exclude contact between the root surfaces and gingival epithelium and gingival connective tissue and permit migration to the root surfaces of PDL cells after surgery, the membrane being constructed substantially of a non-toxic, non-immunogenic, bio-absorbable material.

BRIEF DESCRIPTION OF THE DRAWING

FIG. 1 is a perspective view of the surgical implant article of the present invention.

DETAILED DESCRIPTION OF THE INVENTION

Figure 1A:
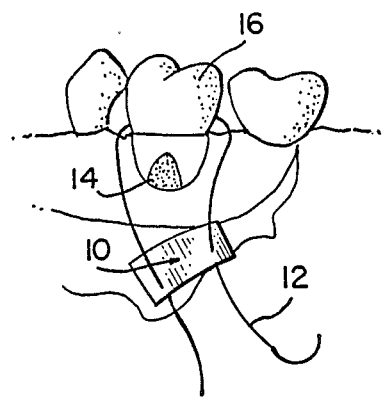
In FIG. 1a, the article is shown loosely placed for covering an exposed root surface in a tooth.

The present invention is predicated on the discovery that the utilization of bio-absorbable materials as surgical implant articles for guided periodontal tissue regeneration and periodontal surgical methods utilizing these materials to prevent contact between the root surfaces and gingival epithelium and connective tissue offer at least three advantages over previously employed materials and methods.

First, the use of bio-absorbable materials eliminates the necessity for a second surgical procedure inasmuch as the material is absorbed by the body after regeneration of the periodontal connective tissue. The avoidance of a second surgery greatly facilitates the periodontal surgical technique, lessening both the expense thereof as well as the discomfort to the patient of a second operation.

Secondly, the bio-absorbable materials employed to construct the articles of the invention result in the formation of significantly greater attachment and bone than those employed heretofore.

Finally, the materials employed to prepare the articles of the invention are non-immunogenic and non-toxic, unlike many of the articles utilized previously.

Any non-immunogenic, non-toxic, bio-absorbable material may be employed to prepare the surgical implant articles of the present invention. The term "bio-absorbable" is intended to include any natural or synthetic solid material capable of being formed into a shaped membrane which is ultimately degraded by the periodontal environment and absorbed by the body after formation of the periodontal connective tissue.

The article is preferably porous to allow an influx therethrough of nutrients to the regenerating periodontal connective tissue fibers. Generally, pores of a size of from about $10\mu$ to about $500\mu$ are sufficient to achieve these purposes.

The membrane may be any desired shape and size to achieve the intended guided tissue regeneration required in any particular application. Generally, it is preferred to utilize membranes having a thickness of from about $50\mu$ to about $200\mu$.

Although any non-immunogenic, non-toxic, bio-absorbable material may be used, it has been found that polylactic acid; polycaprolactone; polyglycolic acid; polyanhydrides, e.g., polyterephthalic acid/sebaic acid anhydride, polydioxanone, polyamino acids, e.g., polyglycine, etc., copolymers of lactic acid with co-monomeric materials such as glycolic acid, hexamethyl sebacic acid, etc., combine the best qualities of nonimmunogenicity, non-toxicity and an acceptable rate of bio-absorption vs. regeneration of periodontal connective tissue and are preferred to prepare the surgical implant articles of the invention. Collagen and other polymers of biological origin (alginates, starch, etc.) are also suitable but have a potential of being immunogenic. Modified natural polymers such as gelatin, oxidized cellulose, etc., may also be utilized.

Additives may be incorporated in the membrane materials such as plasticizers. e.g., citrate esters, hexametholsebacate, etc.; antibiotics, e.g., tetracyclines, penicillins, mefronidazole, clindamycin, etc., to prevent infection of wound area; calcification inhibitors, e.g., ethane hydroxydiphosphonate to inhibit ankylosis in the early stages of healing and periodontal ligament cell growth factor.

The invention is illustrated by the following non-limiting examples.

EXAMPLE 1

Two mongrel dogs were used in the following procedure. During all surgical procedures the animals were sedated with intravenous Pentobarbitol ®. Mucoperiosteal flaps were raised buccal of the second, third and fourth premolars. Along one root in each of these three teeth the buccal and proximal alveolar bone was removed to approximately 25% of its original level. The roots were carefully planed to remove the cementum. The membrane was adjusted to cover 16 of the 24 exposed root surfaces. The membrane extended from mid-crown level to about 1mm apical to the reduced bone crest and was secured to the crown using Scotchbond$^{TM}$ dental adhesive and Silar$^{TM}$ restorative resin. In 8 of the experimental teeth a Millipore ® filter was used and in 8 teeth a polylactic acid membrane was used. A crude preparation of commercially available polylactic acid was dissolved in chloroform and cast on a glass slide to a thickness of 70 µm. The remaining 8 teeth did not receive a membrane and served as controls. The flaps were repositioned and secured with proximal sutures. The sutures were removed after 20 days. During a 2 month long period following surgery the animals were subjected to plaque control by topical application of 0.2% chlorhexidin digluconate 5 times a week. After 2 months of healing the animals were sacrificed by an overdose of Pentobarbital ® and block sections were taken from experimental and control teeth. The specimens were fixed in 10% buffered formalin, decalcified in trifluoroacetic acid (5%) and EDTA (18%), dehydrated and embedded in paraffin. Buccolingual sections of each specimen were prepared with the microtome set at 8 µm. The sections were stained in hematoxylin-eosin. From each root 5 sections 80 µm apart and representing the mid-buccal portion of the root, were used for microscopic evaluation and histometric assessments using 40× magnification. The following linear distances were assessed in mm and mean values of each parameter calculated from the 5 sections of each root.

1. The cementoenamel junction (CEJ) to the apical extension of root planing (aRP)
2. aRP to the coronal level of newly formed cementum (cC).
3. aRP to the crest of the alveolar bone (BC).
4. CEJ to the gingival margin (GM).

The results of the histometric measurements are set forth in Table 1. All of the roots covered with the polylactic acid membrane exhibited newly formed cementum with inserting collagen fibers and newly formed bone. The length of the newly formed connective tissue (aRP-cC) was 2.5 ±0.8 mm with a range from 1.4 to 4.1 mm corresponding to an average of 46% of the length of the curetted root portion (CEJ-aRP). This distance was 5.4 ±1.2 mm (range 3.5–7.6 mm). In the mid section of one block an alkylosis was seen. Coronal regrowth of alveolar bone had occurred adjacent to the roots. The regrowth (aRP-BC) amounted to 2.1 ±1.5 mm (range 0.8–5.3 mm). New connective tissue attachment was seen in 6 out of 8 roots covered with Millipore ® filters. The average length of this attachment (aRP-cC) was 1.4 ±1.0 mm (range 0.0–2.5 mm) which corresponds to 25% of the instrumented root surface The average regrowth of bone (aRP-BC) amounted to 1.7 ±1.4 mm (range 0.0–4.1). In the control roots a limited amount of new attachment was seen in the bottom of the defects in 4 out of 8 roots. The average length of this attachment was 0.7 ±0.9 mm (range 0.0–2.7 mm) which is equal to 12% of the instrumented root surface On the average 0.8 ±1.2 mm (range 0.0–3.0 mm) new bone was seen in the control roots. Root resorption was seen in 4 of the control roots The average length of gingival recession (CDJ-GM) was 0.9 ±0.9 mm in the roots covered with the Millipore ® filter compared to 0.6 ±0.6 mm and 0.5 ±0.7 mm in the control and polylactic acid membrane group, respectively. During the initial phase of healing the gingival margin in the Millipore ® group was consistently more inflamed than in the control group and polylactic acid group.

TABLE 1

Results of histometeric measurements after 2 months of healing. CEJ = cemento-enamel junction; aRP = apical extension of root planing; cC = coronal level of newly formed cementum; BC = alveolar bone crest; GM = gingival margin; S.D. = standard deviation.

| | Polylactic acid | | | Millipore ® | | | Control | | |
|---|---|---|---|---|---|---|---|---|---|
| | Mean (mm) | S.D. | Range | Mean (mm) | S.D. | Range | Mean (mm) | S.D. | Range |
| CEJ-aRP | 5.4 | 1.2 | 3.5–7.6 | 5.5 | 1.5 | 3.0–7.0 | 5.7 | 1.9 | 3.7–8.6 |
| aRP-cC | 2.5 | 0.8 | 1.4–4.1 | 1.4 | 1.0 | 0.0–2.5 | 0.7 | 0.9 | 0.0–2.7 |
| aRP-BC | 2.1 | 1.5 | 0.8–5.3 | 1.7 | 1.4 | 0.0–4.1 | 0.8 | 1.2 | 0.0–3.0 |
| CEJ-GM | 0.5 | 0.7 | −0.5*–1.2 | 0.9 | 0.9 | −0.3*–2.1 | 0.6 | 0.6 | 0.0–1.8 |

*Gingival margin apical to the CEJ

These results show that during a healing period of two months it was possible to obtain a regeneration of on the average 46% of lost connective tissue attachment using guided tissue regeneration with a polylactic acid membrane. The regeneration was significantly less (25%) when using Millipore ® filters to guide the tissue. Magnusson et al, supra, reported that when using Millipore ® filters on surgically denuded root surface in monkeys a new connective tissue attachment that covered on the average 50% of the initial defect was formed. The difference may reflect that the anatomy of the monkey teeth is more favorable for healing. In one of the roots covered with a membrane alkylosis was seen in the mid-portion of the root. Coronal of this area a normal looking periodontal ligament is seen. A likely explanation is that at the area of ankylosis has migrated in horizontally from the mesial and distal part of the defect. Anklyosis development when alveolar bone is in direct contact, with a root surface has earlier been reported [Karring et al, *J. Clin. Periodontol, Vol.* 7, p. 96 (1980)] and is consistent with the theory that the type of attachment formed is determined by the cells that first reach the wound area [Isidor et al, *J. Clin. Periodontol*, Vol. 12, p. 728 (1985); Melcher, *Arch. Oral Biol.*, Vol. 15, p. 1183 (1970)]. Thus, regeneration of cementum and periodontal ligament is achieved only by cells derived from the periodontal ligament [Line et al, *J. Periodontol*, Vol. 45, p. 725 (1974); Melcher, *In Biology of the Periodontium*, ed. Melcher et al, London,- Academic Press, p. 497 (1969); Boyko et al, *J. Periodont. Res.*, Vol. 16, p. 73 (1981); Nyman et al, *J. Clin. Periodontol*, Vol. 7, p. 394 (1980); and Isidor et al, *J. Clin. Periodontol*, Vol. 13, p. 145 (1986). In the present study half of the control teeth demonstrated root resorption This has earlier been observed by several investigators as a consequence after failure of the junctional epithelium to migrate apically [Line et al, supra; Nyman et al, supra; Karring et al, *J. Clin. Periodontol*, Vol. 7, p. 96 (1980); Andreason, *J. Periodont. Res.*, Vol. 16, p. 228 (981)]. The results support the hypothesis that granulation tissue derived from the alveolar bone or the gingival connective tissue induces the resorption when the root surface is not protected by periodontal ligament or the junctional epithelium [Nyman et al, supra; Andreason, supra; and Linde et al, *J. Clin. Periodontol*, Vol. 11, p. 33 (1984)]. In some of the control specimens a limited regeneration was seen, similar to that described by Karring et al [*J. Clin. Periodontol*, Vol. 12, p. 51 (1985)] in teeth with a reduced but healthy periodontal ligament and by Caton and Nyman [*J. Clin. Periodontol*, Vol. 7, p. 212 (1980)].

Figure 1B:
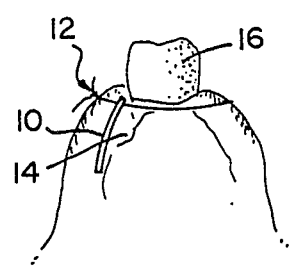
FIG. 1b shows the implant sutured in place over the exposed root surface.

In the drawing, FIG. 1 depicts a typical surgical implant article 10 according to the present invention having sutures 12. In FIG. 1a, the article is shown loosely placed for covering exposed root surface 14 in tooth 16. FIG. 1b shows the implant 10 sutured in place over the exposed root surface 14.

We claim:

1. A method of enhancing the regeneration of periodontal connective tissue at root surfaces exposed by peridontal surgery comprising covering said exposed root surfaces with a membrane which excludes contact between said root surfaces and gingival epithelium and gingival connective tissues and permits migration to said root surfaces of PDL cells after surgery, said membrane having pores therein of a size of from about $10\mu$ to about $500\mu$ and a thickness of from about $50\ \mu$ to about $200\mu$ and being constructed substantially of a non-toxic, non-immunogenic, bio-absorbable material.

2. The method of claim 1 wherein said material is polylactic acid or a copolymer of lactic acid with a member selected from the group consisting of glycolic acid, hexamethylsebacic acid, caprolactone and hydroxybutyrate.

3. The method of claim 2 wherein said material is polylactic acid.

4. The method of claim 2 wherein said material is a copolymer of lactic acid and glycolic acid, hexamethylsabacic acid, caprolactone or hydroxybutyrate.

5. The method of claim 1 wherein said material is collagen.

6. The method of claim 1 wherein said material is polycaprolactone, polyglycolic acid, a polyanhydride, polydioxanone, or a polyamino acid.

7. The method of claim 1 wherein said material additionally contains an effective amount of a plasticizer.

8. The method of claim 1 wherein said material additionally contains an effective amount of an antibiotic, calcification inhibitor or periodontal ligament cell growth factor.

* * * * *

UNITED STATES PATENT AND TRADEMARK OFFICE
CERTIFICATE OF CORRECTION

PATENT NO. : 4,961,707

DATED : October 9, 1990

INVENTOR(S) : Ingvar MAGNUSSON, ET AL

It is certified that error appears in the above-identified patent and that said Letters Patent is hereby corrected as shown below:

In column 1, below the title of the invention, insert the following:

-- This invention was made with government support under Grant No. 2-S07-RR05728-14 awarded by the National Institutes of Health. The government has certain rights in and to the invention claimed in this patent. --

Signed and Sealed this

Fifth Day of October, 1993

*Attest:*

BRUCE LEHMAN

*Attesting Officer*     Commissioner of Patents and Trademarks